United States Patent
Kokko et al.

(10) Patent No.: US 8,248,610 B2
(45) Date of Patent: Aug. 21, 2012

(54) WEB MEASUREMENT

(75) Inventors: Tero O. Kokko, Tampere (FI); Markku Mäntylä, Kangasala (FI); Mikko V. Heikkilä, Pirkkala (FI); Pekka Suopajärvi, Oulu (FI); Marko Toskala, Orivesi (FI); Antti Heikkinen, Helsinki (FI)

(73) Assignee: Metso Automation Oy, Helsinki (FI)

( * ) Notice: Subject to any disclaimer, the term of this patent is extended or adjusted under 35 U.S.C. 154(b) by 305 days.

(21) Appl. No.: 12/524,999

(22) PCT Filed: Mar. 12, 2008

(86) PCT No.: PCT/FI2008/050114
§ 371 (c)(1),
(2), (4) Date: Jan. 21, 2010

(87) PCT Pub. No.: WO2008/110667
PCT Pub. Date: Sep. 18, 2008

(65) Prior Publication Data
US 2010/0165344 A1    Jul. 1, 2010

(30) Foreign Application Priority Data
Mar. 13, 2007  (FI) .................................. 20075174

(51) Int. Cl.
*G01N 21/84* (2006.01)
(52) U.S. Cl. ........................................................ 356/429
(58) Field of Classification Search .................. None
See application file for complete search history.

(56) References Cited

U.S. PATENT DOCUMENTS

| | | | |
|---|---|---|---|
| 4,197,584 A * | 4/1980 | Blazek | 356/394 |
| 4,289,964 A | 9/1981 | Baker | |
| 4,748,400 A | 5/1988 | Typpo | |
| 4,786,817 A | 11/1988 | Boissevain et al. | |
| 5,071,514 A | 12/1991 | Francis | |
| 5,327,770 A | 7/1994 | Hindle | |
| 6,080,278 A | 6/2000 | Heaven et al. | |
| 6,099,690 A | 8/2000 | Hu et al. | |
| 6,452,679 B1 * | 9/2002 | Workman, Jr. | 356/429 |
| 2002/0085201 A1 | 7/2002 | Shakespeare et al. | |
| 2003/0222219 A1 | 12/2003 | Almi et al. | |
| 2004/0069059 A1 | 4/2004 | Shakespeare | |
| 2006/0028213 A1 | 2/2006 | Typpo et al. | |
| 2007/0005525 A1 | 1/2007 | Collette, III et al. | |

FOREIGN PATENT DOCUMENTS
EP    1 391 553 A1    2/2004
* cited by examiner

Primary Examiner — Tu Nguyen
(74) Attorney, Agent, or Firm — Oliff & Berridge, PLC

(57) ABSTRACT

One measuring part of a traversing measuring unit measures at least one characteristic of a web with a first radiation type from a plurality of measuring locations during a traversing movement at successive moments in time. At least two measuring parts of an array measuring unit measure at least one characteristic of the web with another radiation type during each traversing movement at a plurality of different moments in time by directing the measurement to a plurality of measuring locations in the web at each moment in time. A signal processing unit is arranged to estimate at least one characteristic measured by the traversing measuring unit with at least one measurement of the array measuring unit.

34 Claims, 6 Drawing Sheets

WEB MEASUREMENT

FIELD

Figure 1:
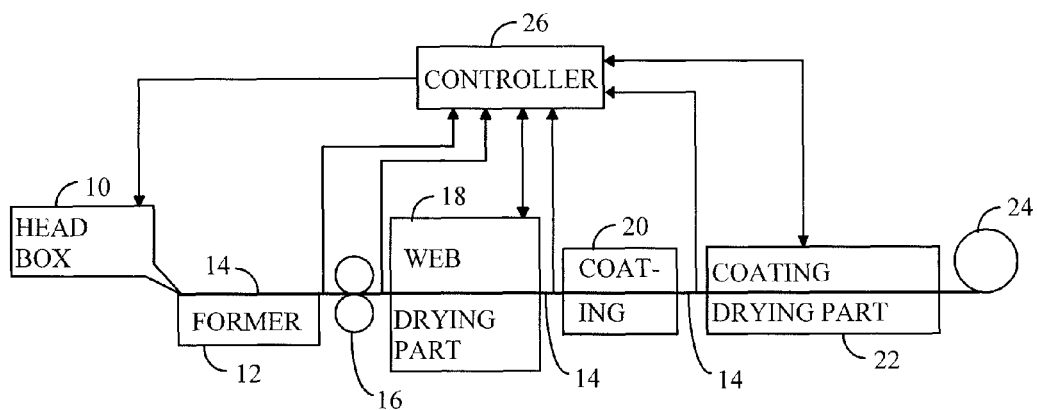

The invention relates to a measuring method, a measuring device, a method of controlling a process and a control apparatus for measuring a web and for controlling a process.

BACKGROUND

In the manufacturing process of paper, a web can be measured by using a sensor unit scanning transversely across the web and a sensor array that is disposed transversely across the web and may be arranged stationary. The characteristics usually measured from a web include moisture content and basis weight. The dry matter content is computationally generated by subtracting moisture content from basis weight. However, in this case, the filler content, i.e. the ash content, fails to be taken into consideration.

Moisture and the chemical pulp content can be measured by means of the attenuation of optical radiation, and the basis weight can be measured by means of the attenuation of β-radiation. Measurements are often made by measuring moisture by means of the transverse sensor array and by measuring both moisture and basis weight by means of the sensor unit traversing across the web. Since the sensors of the traversing sensor unit can be calibrated when the sensor unit is transferred outside the edge of the web, the measurements of the sensors of the traversing sensor unit may be considered accurate. The sensor array, in contrast, whose sensors are not able no move outside the edges of the web, can be calibrated only during web break. At the same time, the sensors of the sensor array are always subjected to dirtying, for example.

However, a drawback of a sensor unit traversing across a web is that during one complete scanning, the web has usually had time to move as much as over a kilometre. Accordingly, measurements from the same transverse location are obtained at extremely long intervals. In addition, for compensating for random deviations, the measurements of a traversing sensor often have to be averaged for instance across four to ten measurements. However, because of the traversing, cross direction measurement results are not close to each other, but far apart in the machine direction, wherefore the cross direction profile cannot actually be measured with a traversing sensor.

Although a transverse sensor array does measure the web more densely, its measurement results are more inaccurate, since the results of the sensors cannot be calibrated. As components of a large number of sensors, usually components of different qualities have to be selected compared with a traversing sensor array having a smaller number of sensors, and, consequently, for instance financing reasons do not cause restrictions in the selection of components. Overall, this results in the incapability of making the measurement accurately both in the cross direction and in the machine direction.

Attempts could be made to solve the problem by measuring the same characteristic in the same manner with both a traversing sensor unit and a sensor array. The same characteristic may be moisture, for example. This way, the moisture measurements of a sensor array can be calibrated with the accurate moisture measurements of the traversing sensor unit, and the direct transverse moisture profile can be measured densely in the machine direction. Generally speaking, all the desired characteristics could be measured with both a traversing sensor unit and a stationary sensor array.

Problems are associated with this solution, too. The placement of all the desired sensors both in the traversing sensor unit and in the stationary sensor array renders the measurement extremely expensive and complicated.

BRIEF DESCRIPTION

The object of the invention is to implement an improved measuring method, a method of controlling a process, a measuring device and a control apparatus. This is achieved by a measuring method for measuring a web moving in the machine direction with a traversing measuring unit and an array measuring unit, of which the traversing measuring unit comprises at least one measuring part that moves in a direction transverse relative to the machine direction and of which the array measuring unit comprises at least two measuring parts successively in a direction transverse relative to the machine direction. The method further comprises measuring, with the traversing measuring unit, at least one characteristic of the web with a first radiation type from a plurality of measuring locations during the traversing movement at successive moments in time; measuring, with the array measuring unit, at least one characteristic of the web with another radiation type during each traversing movement of the traversing measuring unit at a plurality of different moments in time by measuring the web at each moment in time at a plurality of measuring locations; and estimating at least one characteristic measured by the traversing measuring unit with at least one measurement of the array measuring unit.

The invention also relates to a method of controlling a process, comprising measuring a web moving in the machine direction with a traversing measuring unit and an array measuring unit, of which the traversing measuring unit comprises at least one measuring part that moves in a direction transverse relative to the machine direction and of which the array measuring unit comprises at least two measuring parts in a direction transverse relative to the machine direction. The method further comprises measuring, with the traversing measuring unit, at least one characteristic of the web with a first radiation type at a plurality of measuring locations during the traversing movement at successive moments in time; measuring, with the array measuring unit, at least one characteristic of the web with another radiation type during each traversing movement of the traversing measuring unit at a plurality of different moments in time by measuring the web at each moment in time at a plurality of measuring locations; estimating at least one characteristic measured by the traversing measuring unit with at least one measurement of the array measuring unit; and controlling, based on the estimation result, at least one subprocess effecting at least one characteristic of the web.

The invention also relates to a measuring device comprising a traversing measuring unit and an array measuring unit for measuring a web moving in the machine direction; the traversing measuring unit comprises at least one measuring part arranged to move in a direction transverse relative to the machine direction; the array measuring unit comprises at least two measuring parts successively in a direction transverse relative to the machine direction. One measuring part of the traversing measuring unit is arranged to measure at least one characteristic of the web with a first radiation type from a plurality of measuring locations during the traversing movement at successive moments in time; at least two measuring parts of the array measuring unit are arranged to measure at least one characteristic of the web with another radiation type during each traversing movement at a plurality of different moments in time by directing the measurement to a plurality of measuring locations in the web at each moment in time; and a signal processing unit is arranged to estimate at least one characteristic measured by the traversing measuring unit with at least one measurement of the array measuring unit.

The invention further relates to a control apparatus for controlling a process, the control apparatus comprising a traversing measuring unit and an array measuring unit for measuring a web moving in the machine direction; the traversing measuring unit comprises at least one measuring part arranged to move in a direction transverse relative to the machine direction; the array measuring unit comprises at least two measuring parts successively in a direction transverse relative to the machine direction. One measuring part of the traversing measuring unit is arranged to measure at least one characteristic of the web with a first radiation type from a plurality of measuring locations during the traversing movement at successive moments in time; at least two measuring parts of the array measuring unit are arranged to measure at least one characteristic of the web with another radiation type during each traversing movement at a plurality of different moments in time by directing the measurement to a plurality of measuring locations in the web at each moment in time; a signal processing unit is arranged to estimate at least one characteristic measured by the traversing measuring unit with at least one measurement of the array measuring unit; and a controller is arranged to control, based on the estimation result, at least one subprocess affecting at least one characteristic of the web.

Preferred embodiments of the invention are described in the dependent claims.

The web measurement according to the invention provides a plurality of advantages. For performing dense and accurate measurements from the web, the same measurement does not have to be made with both the traversing sensor unit and the sensor array. This simplifies the measuring apparatus. An additional advantage is accuracy, which is based on the traversing measurement, and speed, which is based on the sensor array measurement.

LIST OF FIGURES

Figure 2:
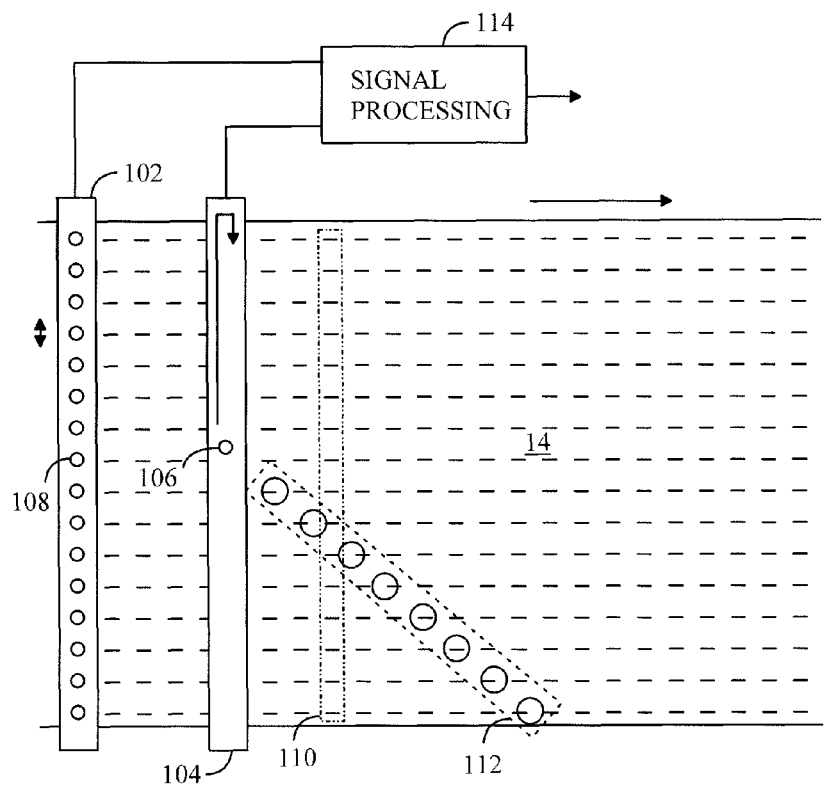
Figure 3:
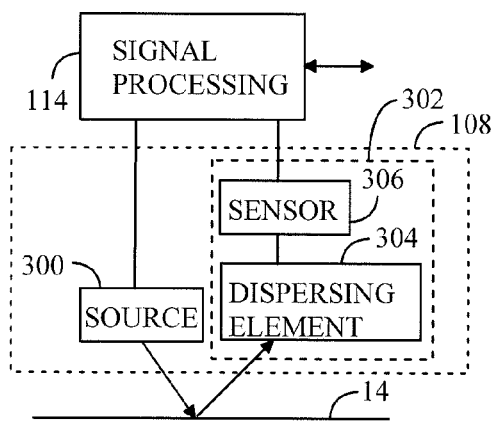
Figure 4:
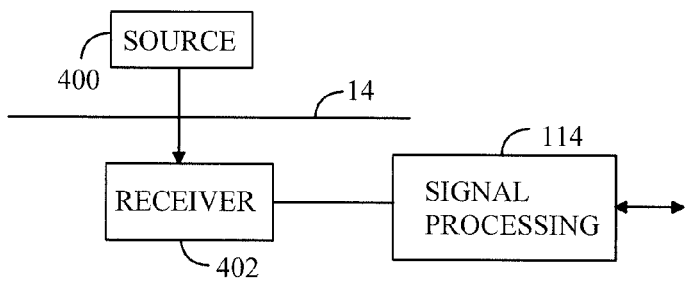
Figure 5:
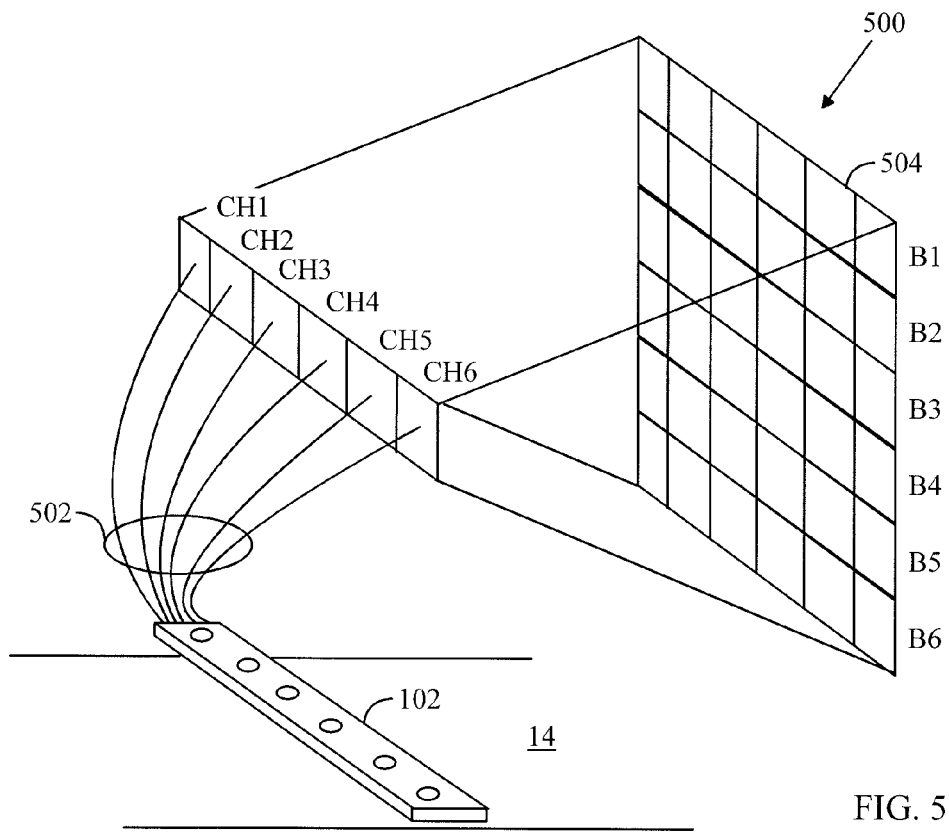
Figure 6:
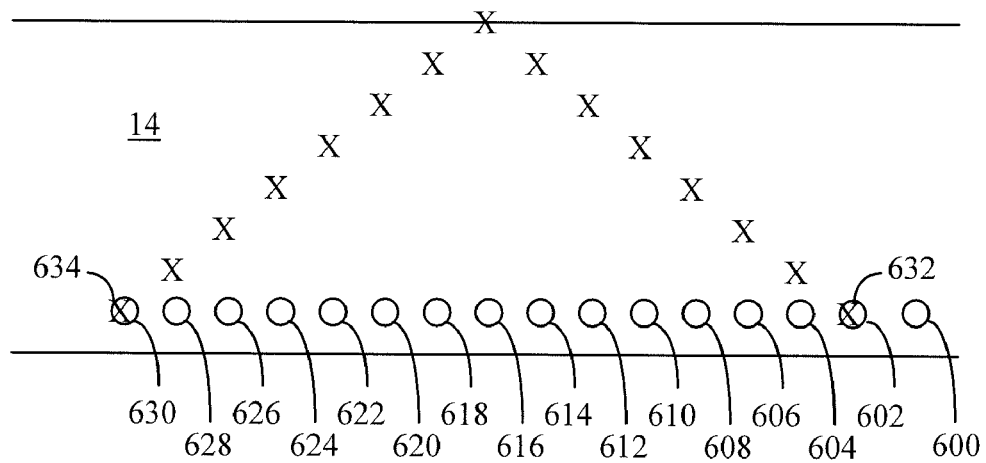
Figure 7:
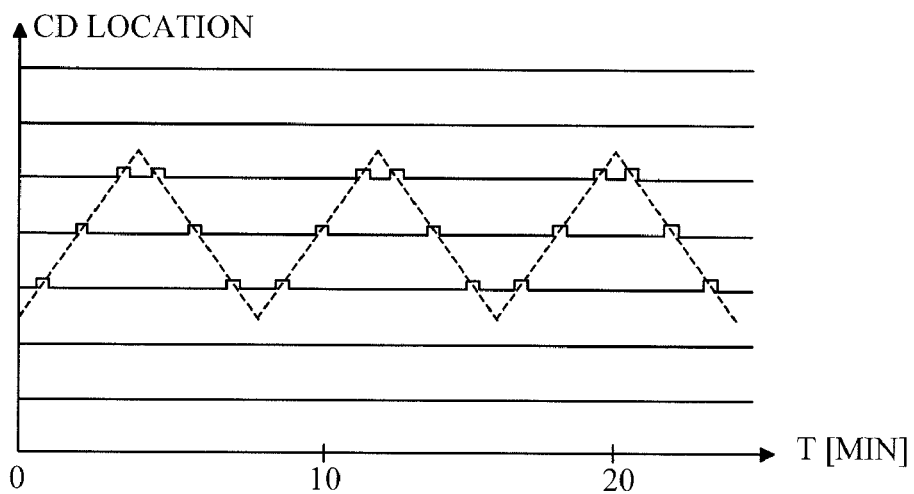
Figure 8:
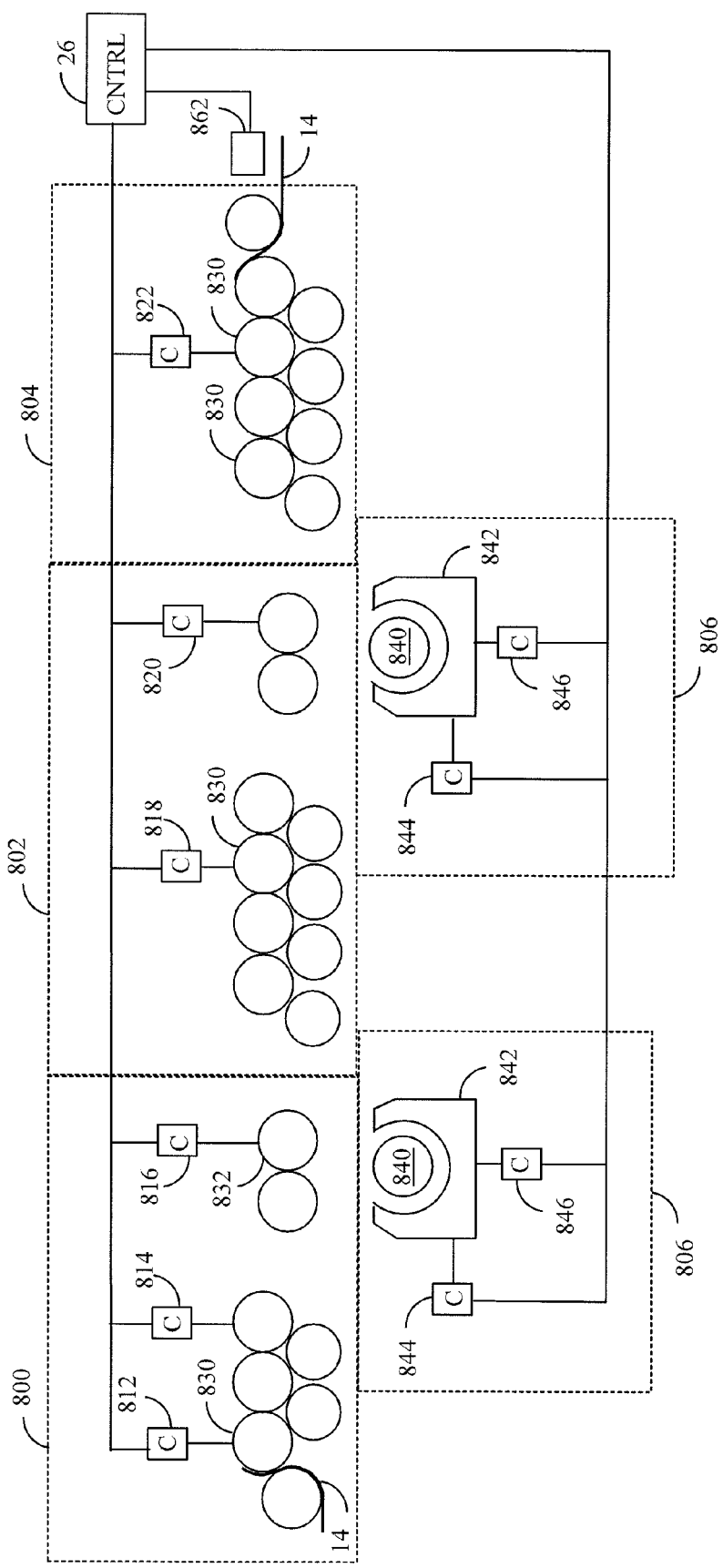
Figure 9:
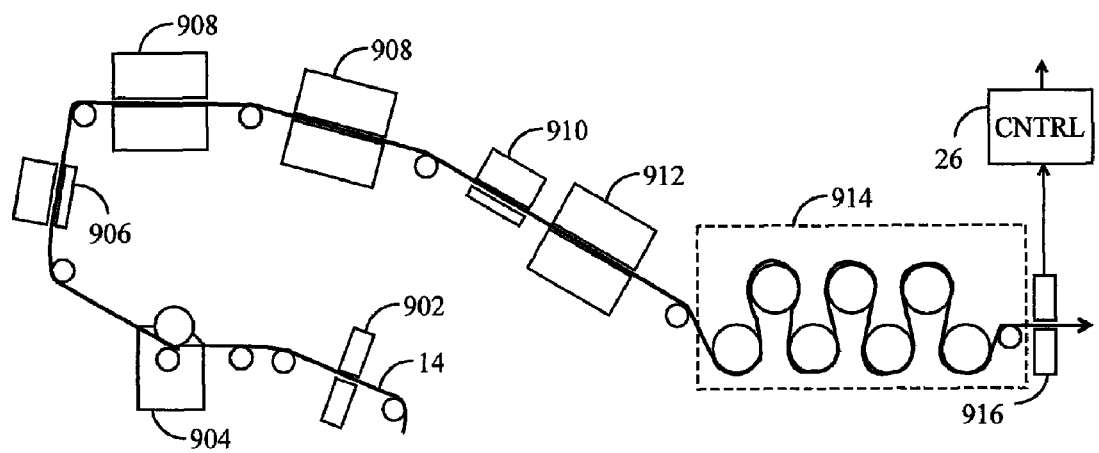
Figure 10:
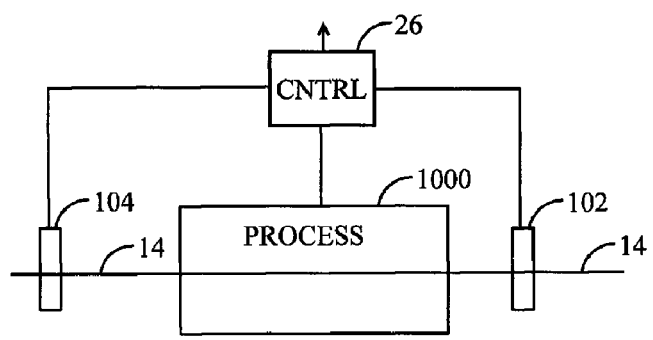
Figure 11:
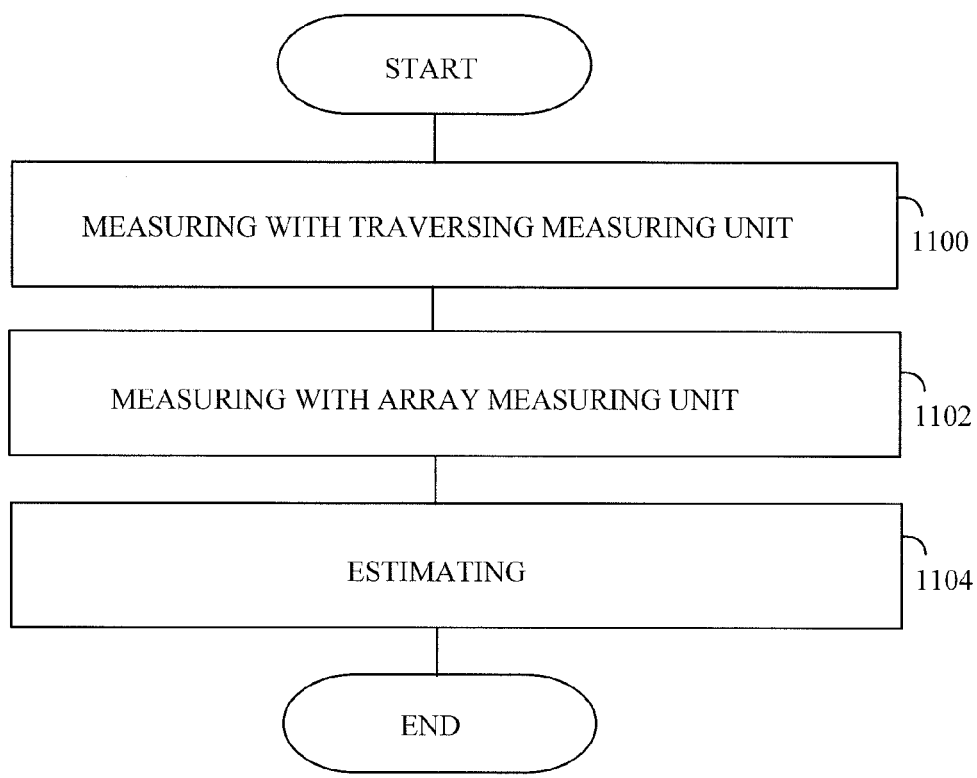
Figure 12:
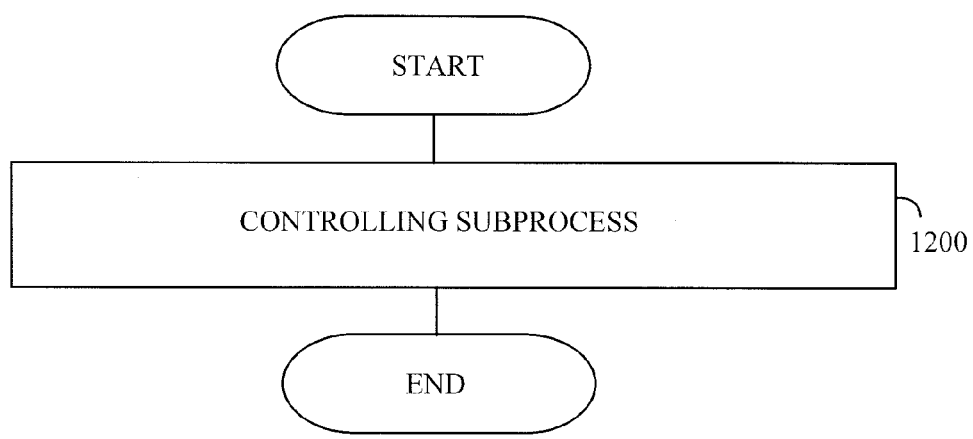

The invention will be described now in connection with preferred embodiments and referring to the attached drawings, in which FIG. 1 shows a paper machine, FIG. 2 shows a measuring device, FIG. 3 shows reflection measurement, FIG. 4 shows transmission measurement, FIG. 5 shows an imaging spectrometer, FIG. 6 shows a comparison of traversing measurement and array measurement, FIG. 7 shows an example of a regular variation in a web characteristic, FIG. 8 shows a drying part of a paper machine, FIG. 9 shows a coating drying part, FIG. 10 shows a measurement relating to a process wherein no dry matter is added, FIG. 11 shows a flow diagram of a measuring method; and FIG. 12 shows a flow diagram of a controlling method.

DESCRIPTION OF EMBODIMENTS

Let us first study the structure of a paper machine by means of FIG. 1. Paper can be manufactured with a paper machine including, among other things, a head box 10. From the head box 10, fibre pulp is fed to a former 12, wherein a paper web 14 is formed from the fibre pulp. After the former 12, the paper web 14 is conveyed to a drying part 18. A compression part 16 may be arranged between the former 12 and the drying part 18. After the drying part 18, the paper web may be conveyed to a coating part 20, after which the coating is dried in a coating drying part 22. Then, the web may be conveyed to a roller 24. The coating part 20 may also be a coating unit separate from the paper machine, wherein the paper web manufactured in the paper machine is coated. The paper machine may also comprise one or more moistening parts, size presses, a surface sizing part and a calender, but these are not shown in FIG. 1. The paper web 14 may be measured at one or more locations between the head box 10 and the roller 24 or after the roller 24, too.

A controller 26 may receive measurement data about the web 14 and control, based on the measurement data, for instance the head box 10, the web drying part 18 and/or the coating drying part 22 in such a manner that the web 14 and, thus the paper to be manufactured, fulfil the desired requirements. In the head box 10, pulp dilution and/or fibre orientation, with which the fibres settle on the wire, may be controlled.

FIG. 2 shows a measuring device for performing measurements. The measuring device may comprise an array measuring unit 102 comprising at least two measuring parts 108 successively in a direction transverse relative to the machine direction (the arrow next to the web 14 shows the movement of the web 14 in the machine direction). In addition, the measuring device may comprise a traversing measuring unit 104. The traversing measuring unit 104, in turn, comprises at least one measuring part 106, which may move in a direction transverse relative to the machine direction. The measurements may be optical and/or based on the measurement of radioactive radiation.

The array measuring unit 102 may comprise a plurality of stationary measuring parts 108. In this case, the array measuring unit 102 may be stationary and comprise fixedly installed measuring parts 108.

Each measuring part 108 of the array measuring unit 102 may move on only part of the width of the web 14 in a direction transverse relative to the machine direction. In this case, the array measuring unit 102 may move in its entirety or each measuring part 108 may move separately. However, the width of the movement of the array measuring unit 102 is narrower than the movement of the traversing measuring part 106. A sufficient width for the movement of the measuring part 108 is the distance between two measuring parts. In other words, if the web 14 is 10 m wide and the array measuring unit 102 comprises 100 measuring parts 108 and the measuring parts 108 are located evenly on the entire width of the web 14, the distance between the measuring parts 108 is 10 cm. In this case, a reciprocating movement having its extreme ends for instance at a 10-cm distance from each other, is sufficient for each measuring part 108. In FIG. 2, such a movement alternative is shown by a short arrow next to the array measuring unit 102.

FIG. 3 shows a measuring part. The measuring part 108 may comprise a source 300 of optical radiation and a detector 302. The source 300 of optical radiation may be for instance a lamp, a LED (Light Emitting Diode) or a laser, and the band of the optical radiation may be wide (hundreds of nanometres or more) or comprise one or more narrow bands (at most dozens of nanometres). The detector 302 comprises a dispersing element 304, such as a prism or a grid (not shown in FIG. 3) for dispersing the optical radiation into a spectrum and detecting with a sensor. The detector 302 comprises, for the detection, for instance one or more sensors 306, sensitive to the optical radiation used, such as a photodiode, a CCD cell (Charge Coupled Device), a MOS cell (Metal Oxide Semiconductor) etc. The sensor 306 may comprise one element, an element row or an element matrix. The sensor 306 may also be imaging, such as a camera.

The source 300 of optical radiation directs optical radiation to the web 14, from where the optical radiation may be reflected to the detector 302. A transmission measurement is also feasible (see FIG. 4). The detector 302 converts the spectrum of the optical radiation received into electrical and transfers the electric signal to a signal processing unit 114 for measuring one or more characteristics from the web 14.

Instead of the source 300 and the detector 302 being located in the immediate vicinity of the web 14, the source 300 of optical radiation may comprise an optical fibre (not shown in FIG. 3) for transferring the optical radiation from the source 300 of optical radiation close to the web 14 and for directing it to the web 14. Accordingly, the source 300 of optical radiation may be located far away from the web 14 (even dozens of metres or further). Correspondingly, the detector 302 may comprise an optical fibre for receiving the optical radiation by the web 14 and for transferring it to the dispersing element and the sensor for the actual detection. The measuring part 106 may also conform to FIG. 3.

The traversing measuring unit 104 may measure the total mass of the web 14 by using β-radiation. FIG. 4 shows this measurement and, therein, a β-source 400 transmits β-radiation through the web to a radiation sensor 402 that detects the strength of the β-radiation received. When the strength of the radiation coming to the radiation sensor 402, without the web 14, is known, the absorption caused by the web 14 may also be measured with such a measurement. The sensor 402 transmits an electrical signal associated with the strength or absorption of the radiation detected to the signal processing unit 114, which may generate a result of the total mass of the web 14 on the basis of the signal. In the same way as in such a measurement performed with β-radiation, also optical radiation may be used in a transmission measurement instead of the reflection measurement shown in FIG. 3. In this case, block 400 corresponds to block 300 and block 402 corresponds to block 302.

The array measuring unit 102 may measure the web 14 by means of optical radiation. This being so, the array measuring unit 102 may measure for instance the mass of the cellulose of the web 14 with optical radiation having a wavelength of about 1,300 to 2,600 nm, for example. The measurement may be based on the determination of the intensity of a single wavelength or the intensities of individual wavelengths. The measurement may also be based on the average intensity of the wavelength band, the intensity distribution of the wavelength band, the average intensities of the wavelength bands or the intensity distributions of the wavelength bands.

FIG. 5 shows an imaging spectrometer 500 that enables the use of each measuring part 108 of the array measuring unit 102 for measuring at least one characteristic of the web 14 simultaneously by means of the spectrum. An optical signal of each measuring part 108 may be transferred, for instance by means of a fibre bundle 502, to a spectrometer 500 gap, which may be constituted by the ends of the fibre bundle 502 themselves, arranged in a row. The gap of the spectrometer 502 may be imaged to an imaging two-dimensional detector 504, the gap of the spectrometer 500 being imaged in the direction of one dimension of the detector (i.e. optical radiations coming from the different measuring parts 108 of the array measuring unit 102), and the spectra of the optical radiation being imaged in the second direction of the detector. The shape of the intensity distribution of the desired band may be measured from the spectrum, the shape being dependent on the characteristic being measured.

The measuring part 106 of the traversing measuring unit 104 may measure at least one characteristic of the web 14 at a plurality of measuring locations 112 at successive moments in time during the traversing movement. The traversing measuring unit 104 may also comprise a plurality of measuring parts that measure at least one characteristic of the web 14. Said one characteristic to be measured may be the total mass $m_{tot}$, the mass of cellulose $m_c$ or the mass of water $m_w$ of the web 14. In addition, the mass of ash $m_a$ may be derived, and it is obtained by subtracting the mass of cellulose and the mass of water from the total mass, $m_a = m_{tot} - (m_c + m_w)$. The first radiation type used in the measurement may be β-radiation or optical radiation on at least one desired band.

The measuring part 106 of the traversing measuring unit may move at intervals outside the web 14, where a reference measurement may be performed. In the reference measurement outside the web 14, an object having known characteristics is measured, and at least one of the results measured therefrom may be compared with a reference result to be obtained when an object having known characteristics is measured, provided the measuring device operates flawlessly. If the result measured differs from the reference result, the traversing measuring unit may calibrated, i.e. fixed for removing changes caused by aging and dirtying, for example, from the measurement results.

At least two measuring parts 108 of the array measuring unit 102 may measure at least one characteristic of the web 14 during each traversing movement at a plurality of different moments in time by measuring the web 14 at each moment in time at a plurality of measuring locations 110. The measuring parts 108 of the array measuring unit 102 may perform the measurements with a different radiation type than each measuring part 106 of the traversing measuring unit 104. In addition, the measurement of the array measuring unit 102 may be directed to the same as or to a different characteristic than the measurement of the traversing measuring unit 104. In the same way as in the case of the traversing measuring unit 104, said one characteristic to be measured may be the total mass, the mass of cellulose or the mass of water of the web 14. The second radiation type used in the measurements may be β-radiation or optical radiation on at least one desired band, but the first and second radiation types may differ from each other. If the first radiation type is β-radiation, the second radiation type may be merely optical radiation. If the first radiation type is optical radiation, the second radiation type may be β-radiation or optical radiation having a different band than the first radiation type.

In said measurements, the total mass, the mass of water and the mass of cellulose may be measured per unit of area. Each value measured may also represent the portion or content of the characteristic measured in the web 14.

FIG. 6 shows a measurement wherein character X refers to measuring locations performed with the traversing measuring unit 104 and O refers to measuring locations 600 to 630 performed with the array measuring unit 102. In FIG. 6, the cross-direction measurements of the array measuring unit 102 are not indicated, only the measuring locations 600 to 630 of one edge are indicated. FIG. 6 shows clearly that the distance 632 to 634 on the web 14 between two traversing measurements directed to the same location in the cross direction may become quite long. No measurement results are obtained from between these measuring locations with the traversing measuring unit 104. However, the array measuring unit 102 measures along the entire width of the web 14 at predetermined intervals or on the desired portion of the web.

The signal processing unit 114 is able to estimate, in the machine direction, at least one characteristic measured by the traversing measuring unit 104 with at least one measurement of the array measuring unit 102. For instance in the case of FIG. 6, this means that if the traversing measuring unit 104 measures the total mass of the web 14, the measurement results of the array measuring unit 102, which may include mass of water, total mass or mass of cellulose, at measuring locations 600 to 630, may be utilized when estimating the total mass of the web (indicated by character X) between the measuring locations 632 and 634.

The estimation may be carried out for instance by the signal processing unit 114 matching the measurement results of the traversing measuring unit 104 with the measurement results of the array measuring unit 102 for the duration of each transverse movement. This enables the correction of the measurement results of the traversing measuring unit 104 to conform with the measurements of the array measuring unit 102.

The traversing measuring unit 104 may measure the total mass of the web 14 and the array measuring unit 102 may measure the water mass of the web 14, i.e. the mass of water in the web 14. In this case, the signal processing unit 114 may estimate the total mass of the web 14 by the measurements of the mass of water by the array measuring unit 102. For example, the total mass may be 80 g/m$^2$ at the measuring location 632 of the traversing measuring unit 104, and the mass of water may be 40 g/m$^2$ at the measuring location 602 of the array measuring unit 102. The measuring locations 632 and 602 may be the same locations in the web 14, but they may also be distinctly different locations. The measuring locations 632 and 602 may be adjacent. Thus, the portion of water in the web is 50%. If, for example, the mass of water at the measuring location 610 is 42 g/m$^2$ instead, the total mass can be estimated to be 42/0.5 g/m$^2$=84 g/m$^2$ for instance on the basis that the proportions of the materials in the web 14 do not change in the short term. As a short term, a period of time ranging from a few seconds to a few minutes, for example, may be considered.

The traversing measuring unit 104 may measure the total mass of the web 14 and the array measuring unit 102 may measure the mass of cellulose in the web 14. In this case, the signal processing unit 114 may estimate the total mass of the web 14 by means of the measurement of the mass of cellulose by the array measuring unit 102. Herein, it may be thought, for example, that the total mass of the web 14 at the measuring location 632 of the traversing measuring unit 104 is measured to be 80 g/m$^2$, and the mass of cellulose at the measuring location 602 of the array measuring unit 102 is measured to be 28 g/m$^2$, corresponding to a 35% portion. If the mass of cellulose is measured to be 27 g/m$^2$ at the measuring location 620 of the array measuring unit 102, the total mass at the location 620 may estimated to be 27/0.35 g/m$^2$=77.1 g/m$^2$.

The traversing measuring unit 104 may measure the total mass of the web 14 and the array measuring unit 102 may measure the mass of cellulose of the web 14 and the water mass of the web 14. This being so, the signal processing unit 114 may estimate the total mass of the web 14 by the measurements of the mass of cellulose by the array measuring unit 102. Herein, it may be thought that the total mass of the web 14 is measured to be 80 g/m$^2$ at the measuring location 632 of the traversing measuring unit 104 and the mass of cellulose of measured to be 28 g/m$^2$ (35%) and the mass of water 40 g/m$^2$ (50%) at the measuring location 602 of the array measurement unit 102. If the mass of cellulose is measured to be 27 g/m$^2$ and the mass of water 38 g/m$^2$ at the measuring point 628 of the array measuring unit 102, the total mass can be estimated by means of the cellulose measurement to be 27/0.35 g/m$^2$=77.1 g/m$^2$, and by means of the water measurement to be 38/0.5 g/m$^2$=76 g/m$^2$. The estimated results of the total mass slightly deviate from each other, but this may in fact improve the estimate. For instance, the total mass at the measuring point 628 is obtained as the average of these two different estimates, being, with one decimal, (77.1 g/m$^2$+76 g/m$^2$)/2=76.5 g/m$^2$. Consequently, in the machine direction, it is possible to detect rapid changes in the different characteristics. Herein, rapid means a solution with which even a plurality of measurements per second may be performed. Correspondingly, rapid changes in the different characteristics may also be detected in the transverse direction.

The traversing measuring unit 104 may measure the mass of water of the web 14 and the array measuring unit 102 may measure the mass of cellulose of the web 14. In this case, the signal processing unit 114 may estimate the mass of water of the web 14 by the mass of cellulose measurements of the array measuring unit 102. Herein, it may be thought by way of example, that at the measuring location 632 of the traversing measuring unit 104, the mass of water of the web 14 is measured to be 38 g/m$^2$, and at the measuring location 602 of the array measuring unit 102, the mass of cellulose is measured to be 28 g/m$^2$. If the mass of cellulose is measured to be 27 g/m$^2$ at the measuring location 620 of the array measuring unit 102, the mass of water at location 620 can be estimated to be (38/28)*27 g/m$^2$=36.6/m$^2$.

The traversing measuring unit 104 may measure the mass of cellulose of the web 14 and the array measuring unit 102 may measure the mass of water of the web 14. In this case, the signal processing unit 114 may estimate the mass of cellulose of the web 14 by the mass of water measurements of the array measuring unit 102. Herein, it may be thought by way of example, that at the measuring location 632 of the traversing measuring unit 104, the mass of cellulose of the web 14 is measured to be 28 g/m$^2$, and at the measuring location 602 of the array measuring unit 102, the mass of water is measured to be 38 g/m$^2$. If the mass of water is measured to be 37 g/m$^2$ at the measuring location 622 of the array measuring unit 102, the mass of cellulose at location 622 can be estimated to be (27/38)*37 g/m$^2$=26.3/m$^2$. If the web 14 comprises only or almost only cellulose, the total mass of the web 14 may naturally also be estimated. In this case, the measurement result 28 g/m$^2$ (35%) of the traversing measuring unit 104 may already act as an estimate of the total mass (28 g/m$^2$/0.35=80 g/m$^2$) and, correspondingly, the measurement result of the mass of water by the array measuring unit 102 may be used to estimate the total mass (26.3 g/m$^2$/0.35=75.1 g/m$^2$).

FIG. 7 shows a regular pattern in the web in the machine direction, caused by a narrow change in the water content of the web 14, caused by a pressure jet. The web shows a saw tooth patterned change in the water content having a cycle length of about 12.5 min. The change pattern is narrow and its water content is about 1% higher than in the environment.

In order for the measurement results of the array measuring unit 102 and the traversing measuring unit 104 to remain reliable, long-term comparisons may be performed on the measurements results thereof. A long term may mean a plurality of minutes. In this case, it is possible to integrate a plurality of successive measurement results of the moving measuring unit 104 that are measured at the same location of the web 14 in the transverse direction. Correspondingly, it is possible to integrate the measurement results of one measuring part 108 of the array measuring unit 102 of the same period and at mainly the same location in the cross direction of the web 14 as the integration of the measurement results of the moving measuring unit 104. Herein, integration may refer for instance to the averaging of the measurement results and it may be performed in the signal processing unit 114, for example. Once both integration results are formed, one measuring part 108 of the array measuring unit 102 may be calibrated by matching the integrated measurement results to correspond to each other. This may also be performed in the signal processing unit 114. Matching the measurement results to correspond to each other may mean for instance that the result of the array measuring unit 102 is corrected to be the same as the result of the moving measuring unit 104. The signal processing unit 114 may perform calibration on each measuring part 108 of the array measuring unit 102. Such an adjustment thus corrects the deviation created between the array measuring unit 102 and the moving measuring unit 104 in the long term.

Web measurements can also be used to control the paper machine. Let us now study the drying of a web, for example. In the drying parts 18, 22 of the paper machine and the coating part, infrared dryers, air dryers and steam pressure cylinders, for example, serve as actuators. Air dryers are on-blowers and through-blowers. The differences of these functional characteristics are in response times and power consumption. The response time $t_{ri}$ of an infrared dryer is in the order of 1 second. The response time $t_{ra}$ of an air dryer is in the order of 1 minute. The response time $t_r$ of a steam dryer is in the order of 2 to 3 minutes.

Let us now study the drying part 18 of a paper machine closer by means of FIG. 8. For the sake simplicity, the web 14 is shown only at the front end and the rear end of the drying part, but naturally, the web 14 continues continuously from one dryer to another through the entire drying part. The drying part 18 of a paper machine may comprise one or more blocks 800 to 804 composed of steam-heated cylinders 830 and underpressure cylinders 832 (all cylinders are not separately denoted by reference numerals) and one or more blowing units 806 serving as an air dryer. The temperature of the cylinders 830 may be controlled by means of controllers 812 to 822. The controllers 812 to 822 obtain their control commands from the controller 26, which may be the same as the signal processing unit 114 or a specific separate block. The on-blowing unit 806 may comprise a cylinder or a roll 840, which may be a suction roll, and a hood 842. The speed of blowing is controlled with a controller 844 and the temperature of the air blast is controlled with a controller 846. The drying part 18 may also comprise one or more through-blowing units (not shown in FIG. 8), wherein hot air is blown from the hood towards the web on the surface of a rectifier roll. The controller 26 controls the drying in accordance with the solution shown by means of the measurement results of the measuring block 862. The blowing can be intensified on the basis of the control in those locations of the web 14, wherein the mass of water in the web 14 is too large (i.e. moisture too high). Correspondingly, the drying can be decreased by means of the control at those locations of the web 14, wherein the web 14 is too dry. Accordingly, for instance the saw tooth pattern caused by excessive moisture in FIG. 7 can be removed from web 14 by increasing drying in the area of the saw tooth pattern.

The effect of the actuators of the drying part 18 can be directed at each particular moment in the cross direction of the web 14 with an inaccuracy $I_e$ of centimetres or dozens of centimetres to the desired area in the web 14. For example, when the web 14 moves at speed v=10 m/s, the inaccuracy in the machine direction may be about 10 m/s*1 s=10 m on an infrared dryer, about 10 m/s*60 s=600 m on an air dryer, and about 10 m/s*180 s=1,800 m on a steam dryer. Of these inaccuracies, the smallest area A of influence of an actuator may be assessed by multiplying web 14 speed v, alignment inaccuracy $I_e$ and response time $t_r$ by each other. In this case, the area A of influence may be about 0.1 m$^2$ to 18 m$^2$ at its most accurate depending on the actuator. The area of influence of an infrared dryer is about 0.1 m$^2$ and it may change locations at intervals of one second to any location in the web 14. On an air dryer, the area of influence is about 6 m$^2$ and it may change locations at intervals of one minute to any location in the web 14. On a steam dryer, the area of influence can be about 18 to 180 m$^2$ and it may change locations at intervals of about three minutes to any location in the web 14.

Let us still study the drying part 22 of paper coating by means of FIG. 9. In the present application, the web and its coating may be understood to constitute the web 14. In the drying part, the web 14 may be measured in the above-described manner in a measuring block 902. The web 14 may be then coated with a coating by using a coater 904. The coating may be dried in the example of FIG. 9 with infrared dryers 906, 910 and air dryers 908, 912. The coating may then be further dried with steam cylinders 914 and finally, the moisture of the coating may be measured in a measuring block 916. The measurement data may be input in the controller 26, which controls the dryers by means of the measurements data in accordance with the solution presented. In the coating drying part, the effect of the actuators may be directed to the coating of the web 14 in the same way as when only the web 14 is studied in connection with FIG. 8.

In an embodiment shown in FIG. 10, the traversing measuring unit 104 and the array measuring unit 102 may be used to measure a process 1000 executed in a paper machine, wherein no dry matter is added. In this case, the measurements can be performed for instance by measuring the web 14 with the traversing measuring unit 104 before the process and with the array measuring unit 102 after the process 1000. However, the measurements may also be performed by measuring the web 14 before the process 1000 with the array measuring unit 102 and after the process 1000 with the traversing measuring unit 104.

Let us assume that the traversing measuring unit 104 is used for measuring before the process 1000 and the array measuring unit 102 after the process 1000. The traversing measuring unit 104 may be used to measure at least one characteristic of the web 14 from a plurality of measuring locations during the traversing movement at successive moments in time. The array measuring unit 102, in turn, can be used to measure at least one characteristic of the web 14, which may be the same as or different from the characteristic measured by the traversing measuring unit 104, during each traversing movement at a plurality of different moments in time by measuring the web 14 at each moment in time from a plurality of measuring locations. Finally, the mass of water or its change can be estimated by at least one measurement by the array measuring unit 102. The mass of water may be at least one characteristic of the web 14 measured by the traversing measuring unit 104. The traversing measuring unit 104 may measure the mass of water with a first radiation type, which may be β-radiation, for example. The array measuring unit 102 may measure the web 14 with a second radiation type, which may be IR radiation, for example. In this case, the array measuring unit 102 may detect an increase or a decrease in the total mass, which can be used to estimate a change in the mass of water, since no dry matter is added in the process measured. In other words, the change in the total mass corresponds to the change in the mass of water.

When the measurements are performed in another order, the array measuring unit 102 can be used to measure the total mass before the process and the traversing measuring unit 104 may be used to measure the mass of water after the process. In this manner, the total mass of the web 14 may be estimated by adding, to the total mass measured before the process 1000, the mass of water measured after the process 1000.

The process 1000 can constitute the moistening and/or calendering of the web 14, for example. Before the web 14 is moistened, the moisture of the web 14, i.e. the mass of water, may be measured either directly or indirectly by means of a measurement of the total mass, for example. The process 1000 may be associated with the manufacture of magazine printing paper, for example, wherein the base paper is already generated and dried in such a manner that its moisture is about 2 to 3%. Moisture may have been measured by IR measurement. The dry matter mass of the base paper, which may be composed of cellulose mass and potentially filler mass, may be known on the basis of measurements performed already at the manufacturing stage thereof by IR measurement (cellulose mass) or β-measurement (total mass), for example. Measurements performed before the process 1000 not adding dry matter may have been performed with the traversing measuring unit 104.

Let us now study moistening together with calendering. In the moistening process, water may be sprayed to the base paper web 14 on both sides. Usually the aim is to use very little water. The web can then be supercalendered by using a multinip calender. Supercalendering renders the paper as smooth and glossy as desired. After supercalendering, the web may be measured for instance with the array measuring unit 102 that may measure the mass of water and/or the mass of cellulose in the web 14 by IR measurement, for example. β-radiation may also be used for the measurement for determining the total mass. By comparing the mass measured after supercalendering with the pre-measured mass enables the determination of the mass of water or a change therein. If the mass of water is measured before the process 1000 and after the process 1000, the change in the mass of water may be determined by calculating the difference between the measurements. If the total mass is measured before the process 1000 and the total mass after the process 1000, a change in the mass of water may be estimated as the difference between the measurements. If the mass of water before the process 1000 is known or measured, the mass of water after the process 1000 may also be estimated. Correspondingly, also calendaring can be measured instead of supercalendering, and the change of the mass of water occurring therein can be followed.

Once an estimate of the mass of water is usable after the process 1000 not adding dry matter, the paper making process may be controlled with the controller 26 based on the estimate. One or more controllable processes may be a process before the process 1000 not adding dry matter, the process 1000 not adding dry matter or a process after the process 1000 not adding dry matter.

Instead of moistening, such a measurement performed on both sides of the process may also be applied to drying, which was already discussed in FIG. 8. Before the drying process, the total mass of the web 14 may be measured with the traversing measuring unit 104 by β-radiation, for example. In addition, the traversing measuring unit 104 may be used to measure the mass of water by IR radiation, for example.

After the drying process, the array measuring unit 102 may be used to measure the total mass of the web 14 by β-radiation, for example, by means of the traversing measuring unit 104. The mass of water or a change therein can be estimated in the same manner as was described above.

A process associated with a steam box may also be measured in the same way. The steam box may be located in the wire part or the pressing part, and the steam box may be used to heat the web, which results in a decrease in the mass of water.

Other processes not changing the dry matter content may include surface sizing and paper coating at a coating station. Coating is explained in FIG. 9.

The solution presented may also be utilized in grade change, wherein the characteristics of the web 14 and, accordingly, those of the paper being manufactured, change. The change can be implemented rapidly and accurately. Before the grade change, for instance the effect of the steam dryer may be initially decreased to a level suitable for the new grade, but compensate for the total drying effect lost by increasing the on-blowing effect. When it is time for the grade change, the effect of the on-blowing may also be decreased to a level suitable for the new grade. In this manner, the grade change can be performed rapidly, since it is faster to adjust the on-blowing than the steam dryer. Instead of decreasing the effect, the effect may also be increased in a corresponding manner. If a plurality of dryers is in use, the change can be started from the slowest and compensate for the effect change of the slowest one or the slowest ones with at least one more rapidly adjustable actuator until the grade change is actually begun.

FIG. 11 shows a flow diagram of a measuring method. In step 1100, the traversing measuring unit 104 is used to measure at least one characteristic of the web 14 with a first radiation type at a plurality of measuring locations 112 during the traversing movement at successive moments in time. In step 1102, the array measuring unit 102 is used to measure at least one characteristic of the web 14 with a second radiation type during each traversing movement of the traversing measuring unit 104 at a plurality of different moments in time by measuring the web 14 at each moment in time at a plurality of measuring locations 110. In step 1104, at least one characteristic measured by the traversing measuring unit 104 is estimated in the machine direction with at least one measurement by the array measuring unit 102.

FIG. 12 shows a flow diagram of a method. In step 1200, at least one subprocess affecting at least one machine-direction characteristic of the web 14 is controlled on the basis of an estimation result. The subprocess may be web drying in the drying part 18, 22 and/or feed of paper pulp from the head box 10 between the lips to the former 12. In the subprocess associated with the head box 10, the gap of the discharge opening or, zone-specifically, dilution valves may be adjusted.

Although the invention is described above with reference to the examples in accordance with the accompanying drawings, it will be appreciated that the invention is not to be so limited, but it may be modified in a variety of ways within the scope of the appended claims.

The invention claimed is:

1. A measuring method for measuring a web moving in the machine direction with a traversing measuring unit and an array measuring unit, of which
    the traversing measuring unit comprises at least one measuring part that moves in a direction transverse relative to the machine direction and of which
    the array measuring unit comprises at least two measuring parts successively in a direction transverse relative to the machine direction, the method comprising:
    measuring, with the traversing measuring unit, at least one characteristic of the web with a first radiation type from a plurality of measuring locations during the traversing movement at successive moments in time;
    measuring, with the array measuring unit, at least one characteristic of the web with another radiation type during each traversing movement of the traversing measuring unit at a plurality of different moments in time by measuring the web at each moment in time at a plurality of measuring locations; and estimating at least one characteristic measured by the traversing measuring unit with at least one measurement of the array measuring unit.

2. A method as claimed in claim 1, the method further comprising measuring, with the array measuring unit, at least one other characteristic of the web, which is different from the characteristic measured with the traversing measuring unit.

3. A method as claimed in claim 1, the method further comprising measuring the total mass of the web with the traversing measuring unit; measuring the mass of water of the web with the array measuring unit; and estimating the total mass of the web with the measurements of the array measuring unit.

4. A method as claimed in claim 1, the method further comprising measuring the total mass of the web with the traversing measuring unit; measuring the mass of cellulose of the web with the array measuring unit; and estimating the total mass of the web with the measurements of the array measuring unit.

5. A method as claimed in claim 1, the method further comprising measuring the total mass of the web with the traversing measuring unit; measuring the mass of cellulose of the web and the mass of water of the web with the array measuring unit; and estimating the total mass of the web with the measurements of the array measuring unit.

6. A method as claimed in claim 1, the method further comprising measuring the web with the traversing measuring unit by using β-radiation.

7. A method as claimed in claim 1, the method further comprising measuring the web with the array measuring unit by means of optical radiation.

8. A method as claimed in claim 7, the method further comprising measuring the mass of cellulose of the web with optical radiation having a wavelength of 1,300 nm to 2,600 nm.

9. A method as claimed in claim 7, the method further comprising measuring at least one characteristic of the web with different measuring parts of the array measuring unit by means of a spectrum simultaneously by measuring the web with the array measuring unit by using an imaging two-dimensional detector, in the direction of whose one dimension arrive the optical radiations from the different measuring parts of the array measuring unit and in the direction of whose second dimension arrive the spectra of the optical radiation.

10. A method as claimed in claim 1, wherein the array measuring unit comprises a plurality of stationary measuring parts.

11. A method as claimed in claim 1, the method further comprising moving the array measuring unit only on a portion of the width of the web in a direction transverse relative to the machine direction.

12. A method as claimed in claim 1, the method further comprising integrating a plurality of measurement results of the moving measuring unit, which are measured from the same location of the web in the transverse direction;

integrating measurement results of one measuring part of the array measuring unit from the same time and from mainly the same location in the transverse direction of the web as the integration of the measurement results of the moving measuring unit; and calibrating one measuring part of the array measuring unit by matching the integrated measurement results of the different measuring units to conform with each other.

13. A method as claimed in claim 12, the method further comprising performing the calibration for each measuring part of the array measuring unit.

14. A method as claimed in claim 1, the method further comprising measuring with the traversing measuring unit before a process, wherein no dry matter is added, and measuring with the array measuring unit after said process.

15. A method as claimed in claim 1, the method further comprising measuring with the array measuring unit before a process, wherein no dry matter is added, and measuring with the traversing measuring unit after said process.

16. A method as claimed in claim 1, the method further comprising measuring the mass of water before a process, wherein no dry matter is added, and estimating the mass of water or a change thereof on the basis of a measurement performed after said process.

17. A method of controlling a process, comprising measuring a web moving in the machine direction with a traversing measuring unit and an array measuring unit, of which the traversing measuring unit comprises at least one measuring part that moves in a direction transverse relative to the machine direction and of which the array measuring unit comprises at least two measuring parts in a direction transverse relative to the machine direction, the method comprising:

measuring, with the traversing measuring unit, at least one characteristic of the web with a first radiation type at a plurality of measuring locations during the traversing movement at successive moments in time;

measuring, with the array measuring unit, at least one characteristic of the web with another radiation type during each traversing movement of the traversing measuring unit at a plurality of different moments in time by measuring the web at each moment in time at a plurality of measuring locations;

estimating at least one characteristic measured by the traversing measuring unit with at least one measurement of the array measuring unit; and controlling, based on the estimation result, at least one subprocess effecting at least one characteristic of the web.

18. A measuring device comprising a traversing measuring unit and an array measuring unit for measuring a web moving in the machine direction;

the traversing measuring unit comprising at least one measuring part configured to move in a direction transverse relative to the machine direction;

the array measuring unit comprising at least two measuring parts successively in a direction transverse relative to the machine direction, and one measuring part of the traversing measuring unit is configured to measure at least one characteristic of the web with a first radiation type from a plurality of measuring locations during the traversing movement at successive moments in time;

at least two measuring parts of the array measuring unit are configured to measure at least one characteristic of the web with another radiation type during each traversing movement at a plurality of different moments in time by directing the measurement to a plurality of measuring locations in the web at each moment in time; and a signal processing unit is configured to estimate at least one characteristic measured by the traversing measuring unit with at least one measurement of the array measuring unit.

19. A measuring device as claimed in claim 18, wherein the array measuring unit is configured to measure at least one other characteristic of the web, which is different from the characteristic measured with the traversing measuring unit.

20. A measuring device as claimed in claim 18, wherein the traversing measuring unit is configured to measure the total mass of the web; the array measuring unit is configured to measure the mass of water of the web; and the signal processing unit is configured to estimate the total mass of the web with the measurements of the array measuring unit.

21. A measuring device as claimed in claim 18, wherein the traversing measuring unit is configured to measure the total mass of the web; the array measuring unit is configured to measure the mass of cellulose of the web; and the signal processing unit is configured to estimate the total mass of the web with the measurements of the array measuring unit.

22. A measuring device as claimed in claim 18, wherein the traversing measuring unit is configured to measure the total mass of the web; the array measuring unit is configured to measure the mass of cellulose of the web and the mass of water of the web; and the signal processing unit is configured to estimate the total mass of the web with the measurements of the array measuring unit.

23. A measuring device as claimed in claim 18, wherein the traversing measuring unit is configured to measure the web by using β-radiation.

24. A measuring device as claimed in claim 18, wherein the array measuring unit is configured to measure the web by means of optical radiation.

25. A measuring device as claimed in claim 24, wherein the array measuring unit is configured to measure the mass of cellulose of the web by means of optical radiation having a wavelength of 1,300 nm to 2,600 nm.

26. A measuring device as claimed in claim 24, wherein the different measuring parts of the array measuring unit are configured to measure at least one characteristic of the web by means of a spectrum simultaneously in such a manner that the array measuring unit comprises an imaging two-dimensional detector, in the direction of whose one dimension arrive the optical radiations from the different measuring parts of the array measuring unit and in the direction of whose second dimension arrive the spectra of the optical radiation.

27. A measuring device as claimed in claim 18, wherein the array measuring unit comprises a plurality of stationary measuring parts.

28. A measuring device as claimed in claim 18, wherein the array measuring unit is configured to move only on a portion of the width of the web in a direction transverse relative to the machine direction.

29. A measuring device as claimed in claim 18, wherein the signal processing unit is configured to integrate a plurality of measurement results of the moving measuring unit, which are measured at the same location of the web in the transverse direction;
the signal processing unit is configured to integrate measurement results of one measuring part of the array measuring unit from the same time and from mainly the same location in the transverse direction of the web as the integration of the measurement results of the moving measuring unit; and
the signal processing unit is configured to calibrate one measuring part of the array measuring unit by matching the integrated measurement results to conform with each other.

30. A measuring device as claimed in claim 29, wherein the signal processing unit is configured to perform the calibration for each measuring part of the array measuring unit.

31. A measuring device as claimed in claim 18, wherein the traversing measuring unit is configured to measure before a process, wherein no dry matter is added, and the array measuring unit is configured to measure after said process.

32. A measuring device as claimed in claim 18, wherein the array measuring unit is configured to measure before a process, wherein no dry matter is added, and the traversing measuring unit is configured to measure after said process.

33. A measuring device as claimed in claim 18, wherein the measuring device is configured to measure the mass of water before a process, wherein no dry matter is added, and estimate the mass or water or a change therein on the basis of a measurement performed after said process.

34. A control apparatus for controlling a process, the control apparatus comprising a traversing measuring unit and an array measuring unit for measuring a web moving in the machine direction;
the traversing measuring unit comprises at least one measuring part configured to move in a direction transverse relative to the machine direction;
the array measuring unit comprises at least two measuring parts successively in a direction transverse relative to the machine direction, and
one measuring part of the traversing measuring unit is configured to measure at least one characteristic of the web with a first radiation type from a plurality of measuring locations during the traversing movement at successive moments in time;
at least two measuring parts of the array measuring unit are configured to measure at least one characteristic of the web with another radiation type during each traversing movement at a plurality of different moments in time by directing the measurement to a plurality of measuring locations in the web at each moment in time;
a signal processing unit is configured to estimate at least one characteristic measured by the traversing measuring unit with at least one measurement of the array measuring unit; and
a controller is configured to control, based on the estimation result, at least one subprocess affecting at least one characteristic of the web.

* * * * *